United States Patent
Hu et al.

(10) Patent No.: US 7,578,795 B2
(45) Date of Patent: Aug. 25, 2009

(54) SYSTEM AND METHOD FOR VISION EXAMINATION UTILIZING FAULT DETECTION

(75) Inventors: George Z. Hu, Raritan, NJ (US); Vance Marc Zemon, West Nyack, NY (US); Peter Derr, East Windsor, NJ (US)

(73) Assignee: Diopsys, Inc., Pine Brook, NJ (US)

( * ) Notice: Subject to any disclaimer, the term of this patent is extended or adjusted under 35 U.S.C. 154(b) by 1145 days.

(21) Appl. No.: 09/924,265

(22) Filed: Aug. 7, 2001

(65) Prior Publication Data

US 2003/0032894 A1 Feb. 13, 2003

(51) Int. Cl.
*A61B 13/00* (2006.01)
*A61B 5/04* (2006.01)

(52) U.S. Cl. .................. 600/558; 600/544; 600/545

(58) Field of Classification Search ................ 600/558, 600/544, 545
See application file for complete search history.

(56) References Cited

U.S. PATENT DOCUMENTS

| | | | |
|---|---|---|---|
| 4,037,586 A | 7/1977 | Grichnik | |
| 4,861,154 A | 8/1989 | Sherwin et al. | |
| 4,913,160 A | 4/1990 | John | |
| 4,953,968 A | 9/1990 | Sherwin et al. | |
| 5,474,081 A * | 12/1995 | Livingstone et al. | 600/544 |
| 5,517,021 A * | 5/1996 | Kaufman et al. | 250/221 |
| 5,638,825 A | 6/1997 | Yamazaki et al. | |
| 6,044,292 A | 3/2000 | Heyrend et al. | |
| 6,115,631 A | 9/2000 | Heyrend et al. | |
| 6,475,162 B1 * | 11/2002 | Hu | 600/558 |
| 6,629,935 B1 * | 10/2003 | Miller et al. | 600/558 |
| 2001/0049480 A1 * | 12/2001 | John et al. | 600/559 |

OTHER PUBLICATIONS

An Electrophysiological Technique for Assessment of the Development of Spatial Vision, Optometry and Vision Science, vol. 74, No. 9, Sep. 9, 1997.
"Medical Instrumentation: Application and Design", 3rd Edition, by John G. Webster, John Wiley & Sons, New York, 1997.

* cited by examiner

*Primary Examiner*—Max Hindenburg
*Assistant Examiner*—Jeffrey G Hoekstra
(74) *Attorney, Agent, or Firm*—Levisohn Berger LLP (57) ABSTRACT

A system and method for performing a vision examination includes displaying a series of visual stimuli for observation by a patient and detecting the patient's visual evoked potentials in response to the visual stimuli. Electrical signals representative of the visual evoked potentials for each stimulus of each series of visual stimuli displayed is amplified, converted to digitized data, recorded and measured. The measured visual evoked potential data is then evaluated and compared to certain predetermined values in order to detect whether or not the measured data is reliable. Data outside of predetermined ranges of values is considered faulty data. For example, the measured data is compared to a maximum value of the output of an amplifier used to enhance the electrical signals, to a predetermined value of the Fourier component at 60 Hz; and to certain ranges to determine if the measured data are outside of expected limits. The occurrence of such data outside these ranges is faulty data. Upon detecting faulty data, new data can be generated until fault free data is obtained or the examination is terminated.

14 Claims, 7 Drawing Sheets

SYSTEM AND METHOD FOR VISION EXAMINATION UTILIZING FAULT DETECTION

FIELD OF THE INVENTION

The present invention relates generally to the field of medical examination for diagnosis and more particularly, to a system and method for audio and visual testing by detecting and measuring evoked potentials as a result of perceived sensory stimuli. In particular, the invention is directed to a system and method for vision examination using visual evoked potentials and incorporating a fault detection technique for determining the validity of evoked potential data acquired in response to periodic sensory stimuli presented to a patient.

BACKGROUND

It is common in the field of medical examinations to assist in diagnosis to conduct various types of tests, whether conducted within a hospital environment, laboratory or physician's office. Such tests can range from simple patient observation to the use of complex examination and diagnostic equipment in which electrical stimuli are applied to a patient and the resulting electrical response signals from the patient are recorded, measured and analyzed. An electrocardiogram is an example of such an examination and diagnostic test in which electrical response signals from stimuli are recorded and analyzed. Electrocardiogram signals are indicative of a patient's heart condition and may be used to detect a heart attack or other cardiac condition. Another familiar medical diagnostic test is an electroencephalogram which uses stimuli to generate electrical signals from the brain of a patient which can be measured in the form of electrical potentials (referred to as evoked potentials) and which indicate the patient's brain activity. Data recorded from an electroencephalogram test are useful for determining such things as seizures or to assist the physician in the diagnosis of brain damage. Other examination procedures also use evoked potentials for diagnosing a variety of other diseases, including diseases of the central nervous system, auditory system and the visual system. Evoked potentials are typically determined by measuring electrical responses to sensory stimuli. When stimulation is applied to a particular sense of a human being, a corresponding brain potential is evoked at an information processing part of the brain that functions to manage the particular sense. Such evoked brain potentials are usually detected and measured by the use of electrodes positioned on the skin of the human head in the area of the information processing center of the brain corresponding to the particular sense involved.

Visual evoked potentials (VEP) are the evoked potentials in response to visual stimulation and are particularly useful to assist in diagnosing ophthalmic diseases in infants and young children, because such individuals are not always able to indicate responsiveness to visual stimuli or to verbalize the occurrence of vision failure. The retina contains more than 130 million light-receptor cells. These cells convert light into nerve impulses that are processed for certain features, which are transmitted by the optic nerve to the brain, where they are interpreted. Muscles attached to the eye control its movement. Birth defects, trauma from accidents, disease and age-related deterioration of the components of the eye can all contribute to eye disorders. Information processing in the brain is electrochemical in nature. Evoked potentials are the electrical responses of the brain elicited by sensory stimulation. The electrical responses of the brain produced by visual stimulation are visual evoked potentials. Changes in these visual evoked potentials can be used to pinpoint anomalies along the visual pathways. These visual pathways are interconnected linkages of cells, beginning with photoreceptor cells in the retina, passing through horizontal cells, bi-polar cells and amacrine cells to ganglion cells, which wind together to form optic nerve fibers leading to cells in the brain's thalamus which then leads to cells in the visual cortex. The retina does not register images and transmit them, unaltered, to the brain. Instead, it selects and abstracts biologically useful features of information in the patterns, which strike it, and transmits a selectively filtered message to the brain by means of interactions within and among neural networks. Further processing of the information then takes place in the brain by means of similar but more complex interactions in neural networks there. Anomalies in this electrical transmission are variations from the expected pattern in the reaction of cells along the visual pathways. They are believed to provide useful insight into many diseases and conditions affecting the brain, central nervous system, the eye and the ear. Therefore, one way to detect possible visual impairment in infants and small children is to record and measure visual evoked potentials in response to visual stimulation. Visual evoked potential analyzers can be used in screening for diseases and conditions of the brain, central nervous system, the eye and the ear. They detect abnormalities in the functioning of a patient's brain by analyzing the electrical responses of the brain, which occur when certain rapidly changing patterns of light displayed on a video screen, are viewed. These electrical responses are called potentials. Sensors attached non-invasively to the scalp permit measurements of visual evoked potentials and are widely used in basic research in vision and as an aid in the diagnoses of neurological and ophthalmic disorders. However, since these sensors record visual evoked potentials from large areas of the brain, relating changes in these recorded waves to specific neural processes has previously proven difficult or impossible.

Visual evoked potential systems have heretofore been used to test infant response to visual stimuli in order to determine the possible presence of amblyopia. Failure to detect amblyopia as early in life as possible could lead to incurable vision problems in adulthood. However, if detected early, amblyopia can be effectively treated. Accordingly, it has been found desirable to conduct visual evoked potential tests on infants and other humans. One such system, known as the VENUS System, was heretofore commercialized by Neuroscientific Corp. and is described in an article entitled "An Electrophysiological Technique for Assessment of the Development of Spatial Vision," Optometry and Vision Science, Vol. 74, No. 9, Sept. 9, 1997.

Ear infections, or otitis media, are a major reason for doctor visits among preschoolers in the U.S., accounting for more than 24 million trips a year to the family physician. The problem is a serious one with the treatment of children under two years of age for such infections having tripled between 1975 and 1990. Children who suffer from repeated ear infections before age six often experience temporary hearing loss, speech and language delays, coordination difficulties and, in some cases, permanent hearing loss. Likewise many infants, about 4 in 1000 births, have hearing impairment problems that cause delays in speech, language and cognitive development. In many instances, hearing loss is not detected until the child is two to three years old and not speaking properly. The present invention can also be adapted to screen for malfunctions in hearing among infants and children thereby providing early detection for both eye and ear problems.

Visual evoked potentials are measured by detecting electrical signals from electrodes which are attached to the skin of the human patient while displaying visual stimuli to be observed by the patient. The electrical signals, representative of the visual evoked potentials generated in response to sensory perception of the visual stimuli, contain information about the visual sensory capability being processed along the visual neural pathways from the retina to the cortex of the brain. However, the visual evoked potential electrical signals are in the microvolt range, sometimes less than one microvolt, and are sometimes obscured by other random potentials arising in adjacent areas of the brain or as a result of random muscle movement of the head and neck or distraction of the subject. Accordingly, VEP is a signal that has a degree of variability and randomness that may also be a result of the test environment, poor electrode connection, or electromagnetic noise. Such variability and randomness could be of such significance as to render the measured visual evoked potentials useless. Accordingly, before visual evoked potential data is to be relied on for diagnosing a condition of the patient, it is important to determine if the recorded visual evoked potential data is reliable.

OBJECTS OF THE INVENTION

It is accordingly a principal object of the present invention to provide a system and method of inducing, detecting and measuring visual evoked potential data or information in response to visual stimuli presented to a patient, which is reliable for diagnosis and early detection of visual disease or impairment.

Another object of the present invention is to provide a system and method to detect faults in VEP response measurements.

A still further object of the invention is to provide a system and method for performing a vision examination which includes displaying a series of visual stimuli for observation by a patient and detecting electrical signals representing the patient's visual evoked potentials in response to that visual stimuli, and recording and measuring the electrical signals representative of the visual evoked potentials in order to determine if the electrical signals are false indications of those evoked potentials by comparing those signals to predetermined values.

A more specific object of the present invention is to provide a method to determine if a detected VEP signal reaches the maximum value of the output of an amplifier used to enhance the VEP signal when recording the VEP signals, which is an indication that the electrodes are poorly connected.

It is yet a further specific object of the present invention to determine if the Fourier component at 60 Hz exceeds a certain threshold value which would indicate that the impedance between the electrodes and the skin of the scalp is excessive.

A further object of the invention is to provide a means for determining whether the patient has failed to focus on the visual stimulus by determining if there are any abrupt jumps beyond normal ranges in the VEP signal data.

It is still a further object of the present invention to provide means for determining whether there is a bad electrode connection, muscle movement or other brain activity impacting or affecting the detection and measurement of visual evoked potentials by detecting VEP signal drift.

Other objects, features and advantages of the invention will be apparent to those skilled in the art after appreciating the invention from the description hereinbelow.

SUMMARY OF THE INVENTION

The present invention is therefore directed to a system and method for performing a vision examination that includes displaying a series of visual stimuli for observation by a patient and detecting the patient's visual evoked potentials in response to the visual stimuli. Electrical signals, representative of the visual evoked potentials for each stimulus of each series of visual stimuli displayed is converted to digitized data, recorded and measured. The measured visual evoked potential data is then evaluated and compared to certain predetermined values in order to detect whether or not the measured data is reliable. Data outside of predetermined ranges of values is considered faulty data. Specifically, the measured data is compared: to a maximum value of the output of an amplifier used to enhance the electrical signals, to a predetermined value of the Fourier component at 60 Hz; and to certain ranges to determine if the measured data is outside of expected limits, thus indicating unreliable data results. The occurrence of such data outside the predetermined ranges is faulty data. Upon detecting faulty data, new data will be generated until fault-free data is obtained or until it is determined that conditions will not yield reliable data.

The foregoing and other features of the present invention are more fully described with reference to the following drawings annexed hereto.

DESCRIPTION OF THE PREFERRED EMBODIMENTS

Figure 1:
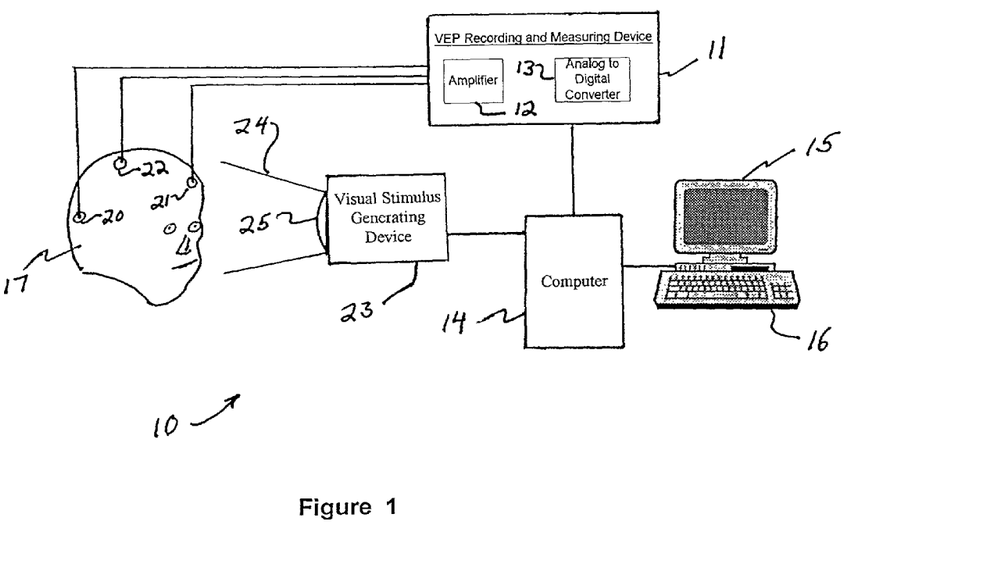
FIG. 1 is a block diagram illustrating the overall architecture of the present invention.

Generally, the system of the present invention incorporates a visual stimulator, data acquisition means with amplifiers to enhance VEP signals and a monitor to view results. Specifically, the system 10 of the present invention, as depicted in FIG. 1, includes a visual evoked potential recording and measuring device (or data acquisition component) 11 coupled to a central processing unit of a computer 14 for controlling the operations and functions of the VEP recording and measuring device 11. VEP recording and measuring device 11 includes an amplifier 12 for enhancing the VEP signals being acquired and an analog to digital converter 13 for converting the signals into a form for digital use. The amplifier is optically isolated for patient safety, has a high common mode rejection ratio, low noise and stability for low signal and frequency application. Computer 14 is coupled to a monitor 15 for displaying the data captured by the VEP recording and measuring device 11 and for providing a means to convey information concerning the operation of a test being conducted on a patient 17 to an operator. Keyboard 16, also connected to computer 14, provides a means to input information to the computer relating to a subject being tested. The responses in the brain to the stimuli are picked up by sensors attached non-invasively to the patient's scalp and are amplified, digitized, recorded and analyzed by the data acquisition component. Disposable electrodes 20, 21 and 22 are positioned on the scalp of the patient 17 over the visual cortex, the frontal cortex, and the parietal cortex, respectively. Electrodes 20, 21 and 22 are connected via hard wire to the VEP recording and measuring device 11. A visual stimulus generating device 23 is also connected to and controlled by computer 14 for generating visual stimuli to be perceived by the patient. A hood 24 may also be used and positioned between the stimulus generating device 23 and the patient 17 in order to enhance attention by the patient to the visual stimulus being displayed. The stimuli are highly variable arrays of one or two-dimensional light patterns. These stimuli can be rapidly modified or varied (i.e. at ~60 Hz or higher frame rate) and luminance contrast and main luminance can be altered through a full range of the gray scales from white to black. By permitting different regions of a pattern to be varied independently or contrasted with a static area, the system can make specific and detailed measurements of visual evoked potentials and perform all of the conventional visual evoked potential tests.

Figure 2:
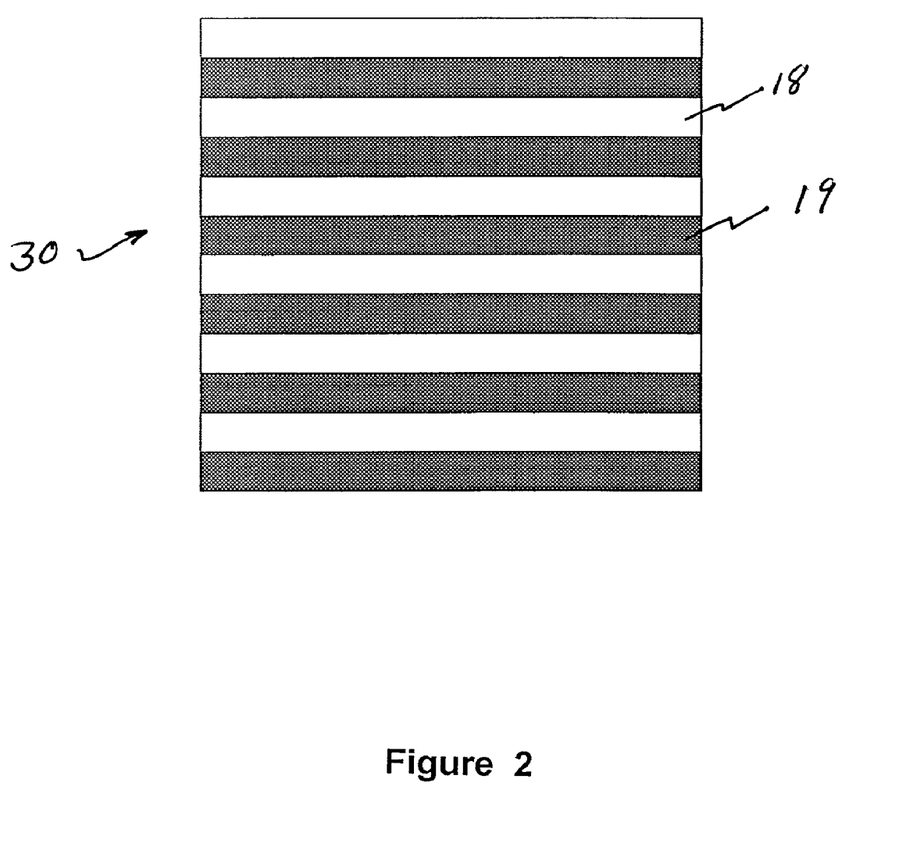
FIG. 2 is an illustration of one type of visual stimulus used in the present invention.

The present invention incorporates software carried by computer 14 for displaying a graphical user interface (GUI) on the monitor 15 upon initiation of the testing procedures. The GUI allows an operator to enter patient data such as name, date of birth, identification number, etc. After the patient data is entered into the system, the vision test will begin with the presentation of visual stimuli on the stimulus display screen 25 of the stimulus device 23 for observation by the patient. The generation of the visual stimuli by device 23 is initiated and controlled by computer 14. The stimuli consists of sweeps of variable spatial patterns in the form of horizontal gratings that vary from thick to thin with the presentation of each such pattern lasting approximately one second. FIG. 2 illustrates an example of the type of stimulus display presented to the patient. The display consists of a pattern 30 of alternating and contrasting horizontally oriented light bands 18 and dark bands 19. The system of the invention causes the stimulus generating device 23 to present a series of patterns on the visual display screen 25. A series typically consists of six different patterns to be displayed. The display of each pattern lasts approximately one second. Each pattern differs from other patterns by the thickness of each band. In presenting the series, the first displayed pattern will have the thickest bands and each successive pattern displayed will have narrower bands. A number of sets of displays (each set consisting of five sweeps of a series) will be presented to the patient for observation by each eye of the patient. A set consists of five sweeps of a series, where a sweep is the continuous consecutive display of the six patterns of a series. By entering commands on an input device, such as keyboard 16 connected to computer 14, an operator may vary the series and sets of displays and after each series or set is complete, the operator can initiate presentation of a next series or set of displays. A set of displays will be presented to each of the eyes of the patient. Tracking information about each visual stimulus display will be presented on monitor screen 15 so that the operator will be able to track display activity. Upon completion of presentation of the sets of visual stimuli, the system of the invention will present the results of the tests on monitor screen 15.

A feature of the invention is the ability of the system to detect faulty responses (i.e., a fault detection capability) in the VEP signal measurements as a result of possible signal drift due to loose connections or bad connections, abrupt jumps in the VEP signal data indicating that the subject has not focused on the stimulus being displayed or that there are outlying data (i.e., the VEP recorded signal data is outside of a predetermined normal distribution). If any signal data is suspected of any of these defects, the system will not use the suspect data in completing an analysis of the VEP response. Rather, the system will generate a message to be displayed on monitor screen 15 to alert the operator of a fault and to cause the operator to continue running sets of stimuli presentations until a minimum number of good sets of data are recorded for each eye. Laboratory experience suggests that reliable data from five sweeps of a series (a set) is usually adequate to draw proper conclusions from the examination.

Figure 3:
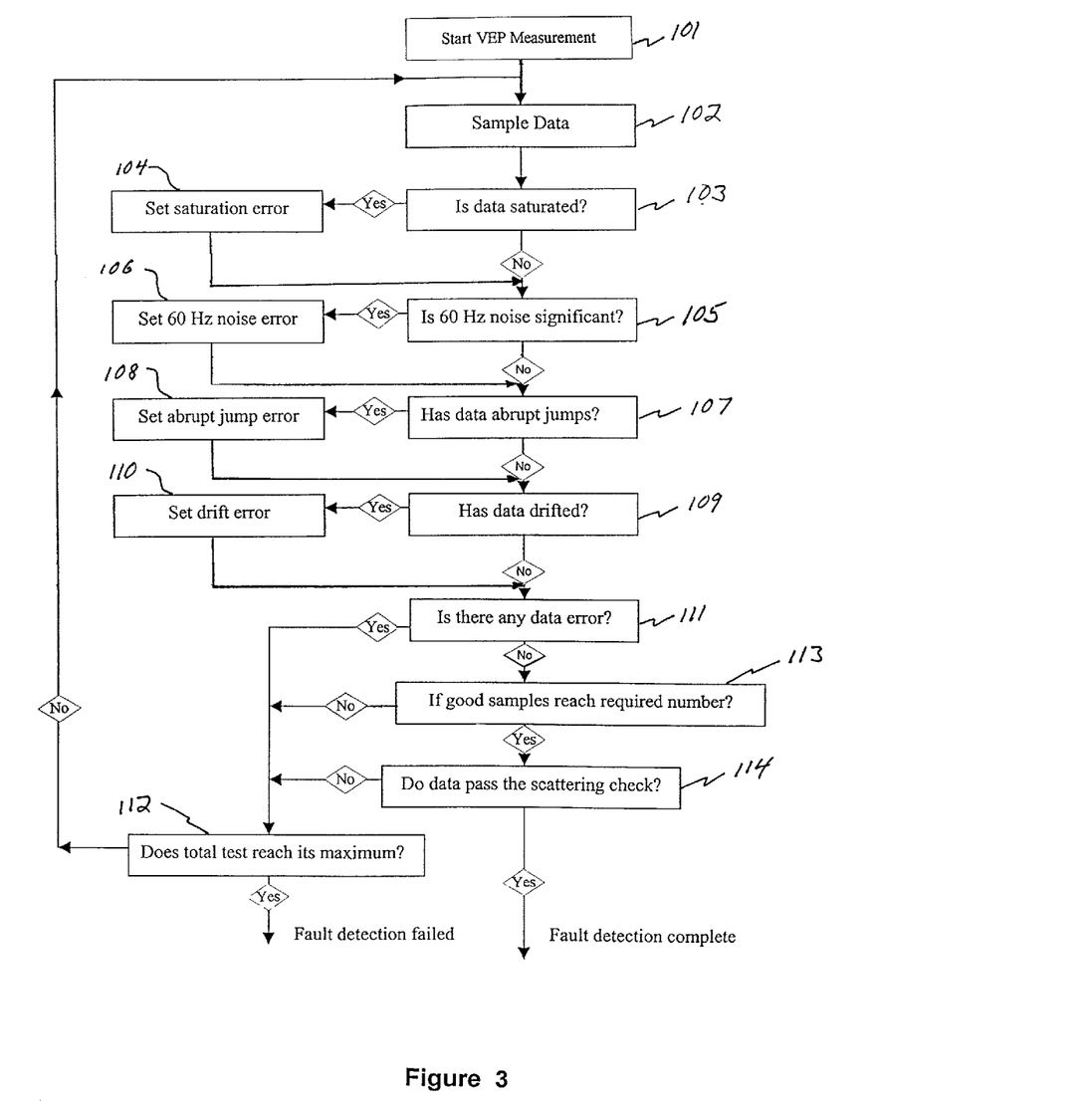
FIG. 3 is a flow chart of the process of the present invention.

FIG. 3 illustrates the process of the invention to determine if the measured VEP signals from the stimulus being displayed contain false indicators, faults or confounds which would result in unreliable data. The first step in the process of determining faulty signal data is the initiation at step 101 of VEP signal measurements. This is usually accomplished by the operator initiating stimulus presentation through a signal generated on keyboard 16 through computer 14. At step 102, sample signal data is first amplified and then recorded by the VEP recording and measuring device 11. Step 103 determines if the VEP signal being recorded reaches a maximum value of the output of the amplifier used in recording the VEP signals thus indicating saturation of the signal and an indication that the electrodes are not properly connected. The electromagnetic noise across the open circuit inputs of the amplifier is usually enough to cause the amplifier to saturate. If the data is saturated, the system will make note of the detected error at the "Set Saturation Error" step 104 for future recall (as discussed below). By setting the saturation error, a message will also be displayed on monitor screen 15 to alert the operator that a saturation error has occurred. This is an indication that the electrodes have a bad connection. When the operator sees this message, he will take the appropriate steps to correct the bad connection. If there is no saturation of the signal, and thus no faulty signal from poorly connected electrodes, the process will proceed directly from step 103 to step 105 without setting or making notation of a saturation error.

At step 105, the process determines whether or not the Fourier component of the VEP measured wave form at 60 Hz (electric noise) exceeds a certain threshold value. A periodic signal can be expressed as a sum of sinusoids with various amplitudes, phases and multiple frequencies. These frequency components are referred to as Fourier components. If the Fourier component at 60 Hz does exceed a predetermined value, it is an indication that the impedance between the electrodes and the scalp of the patient is excessively high. This will lead to bad data. If the 60 Hz noise exceeds the predetermined maximum value, then the system records the error, or "sets" the 60 Hz noise error, at step 106 and proceeds to step 107. Simultaneously, a message is displayed on monitor 15 to alert the operator that the electrodes need attention and possible correction. If the 60 Hz noise is not excessively high, i.e. does not exceed the predetermined value, the system will proceed directly from step 105 to step 107 without recording or making note of a 60 Hz noise error.

Step 107 determines whether or not the VEP data abruptly jumps beyond normal working ranges during the test. If the VEP data is considered beyond a normal working range, it is an indication that the patient had a sudden muscle movement, or the electrodes were moved, or that the system responded to some external electrical event, such as the operation of a nearby electric motor, perhaps from a local elevator. The system will record at step 108 an abrupt jump error, the operator will be notified and the process will move to step 109.

Figure 4:
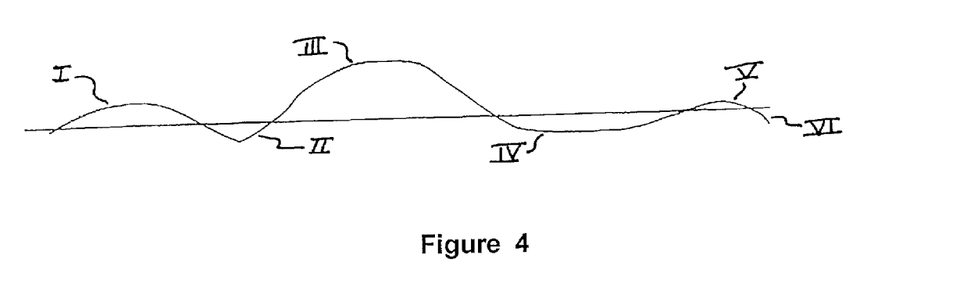
FIG. 4 is an example of a graphical representation of visual evoked potential data acquired during a test procedure.

Step 109 determines VEP slow drift due to poor electrode connection, or possible muscle movement, or other brain activities causing the VEP signal to drift. This step uses a moving average algorithm to smooth out the VEP signals being received over a period of time resulting in a curve of average reserve time and then integrates each segment of the smoothed curve separated by zero crossing points. When the maximum value, after complete segment integration, exceeds a threshold value, the VEP signal is deemed to have a significant drift. FIG. 4 illustrates an example of VEP signal smoothed curve integration. There are six integration values corresponding to six segments of the curve (segments I-VI) separated by zero level crossings. In the example illustrated, the maximum absolute value of the total integrated curve is the one which corresponds to segment III. This is a known technique, such as described in reference book "Medical Instrumentation: Application and Design", $3^{rd}$ Edition, by John G. Webster, John Wiley & Sons, New York, 1997, which is hereby incorporated by reference.

Figure 5:
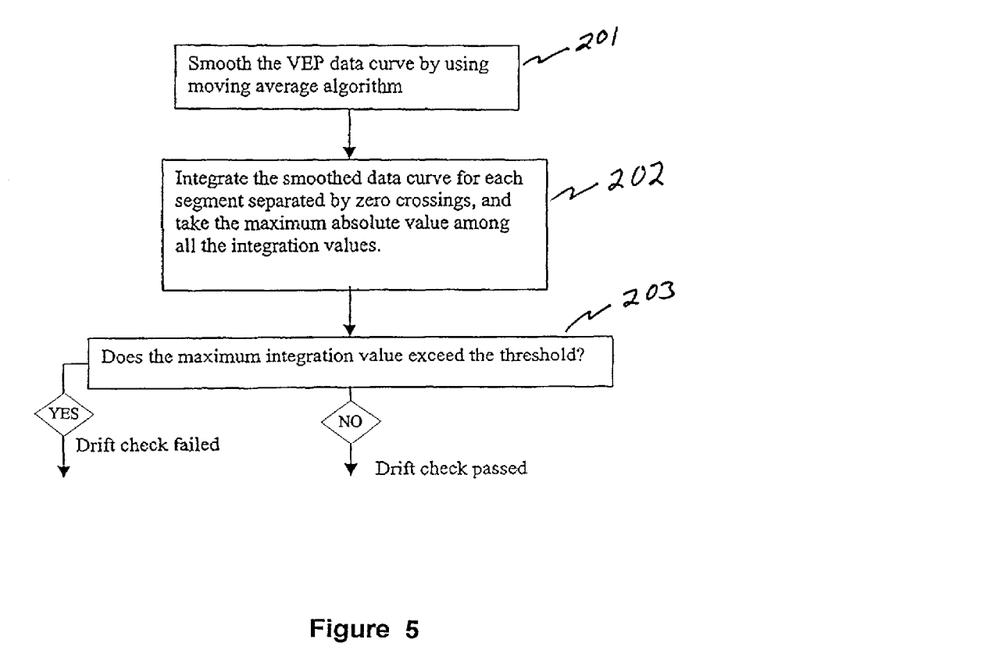
FIG. 5 is a flow chart of the steps of checking for data drift error.

FIG. 5 illustrates the process of checking the signal drift. Step 201 is to smooth the VEP signal data curve by using the moving average algorithm. The next step at 202 is to integrate the smoothed data curve for each segment separated by zero level crossings and to identify the maximum absolute value among all the integration values (such as illustrated in FIG. 4). The check is completed at step 203 by ascertaining whether the maximum integration value exceeds a predetermined threshold. If it does not, then the signal drift check has passed and the process of FIG. 3 proceeds to step 111. If the signal drift check failed, step 110 sets (i.e., records) a drift error, notifies the operator on monitor screen 15, and then proceeds to step 111.

At step 111, there is a determination as to whether or not any data error has been previously noted or recorded at one of the set error steps 104, 106, 108 or 110. If there has been a data error recorded, the process will proceed to step 112 to determine if a predetermined maximum number of data points have been generated during the test. If not, the system will start the VEP measurement procedure again to generate more sets of visual stimuli and more VEP data. The system will then run through the sequence of collecting additional data unless at step 112 the system detects that a predetermined maximum number of data points have been reached. If the maximum has been reached, it is an indication that the conditions for acquiring satisfactory error free VEP signal data is just not achievable at this time and a message will be displayed on monitor 15 to alert the operator that the fault detection process has failed and the acquired data can not be relied upon. If there was no error in the data detected up to step 111, step 113 then determines if there is enough good data samples to reach the required number of error free data samples to have reliable conclusions. If it is determined at step 113 that there are not enough good data samples, then, as described above, step 112 will determine if more data can be generated or if the maximum has been reached.

Figure 6:
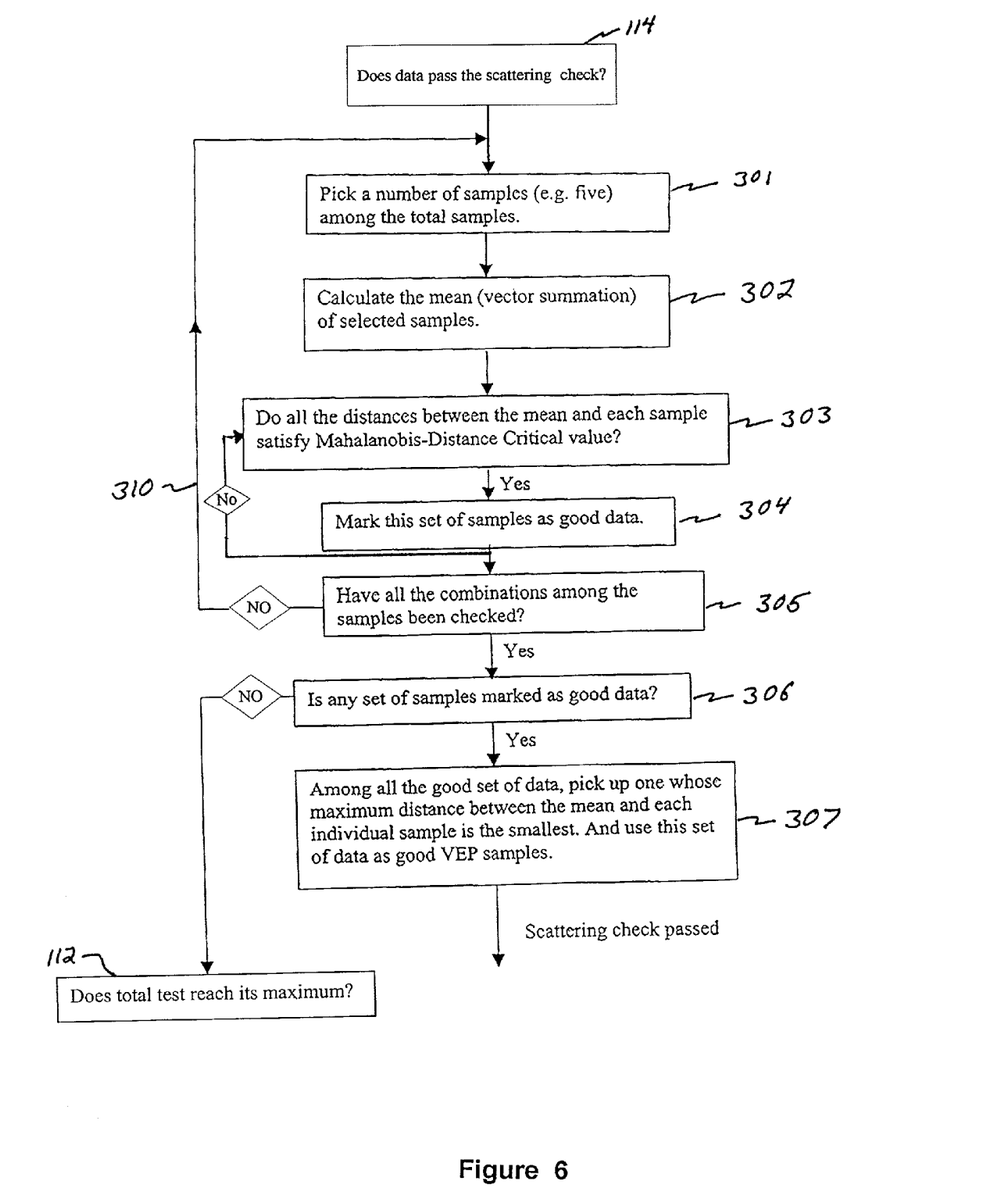
FIG. 6 is a flow chart of the steps for conducting the scattering check of the present invention.
Figure 7:
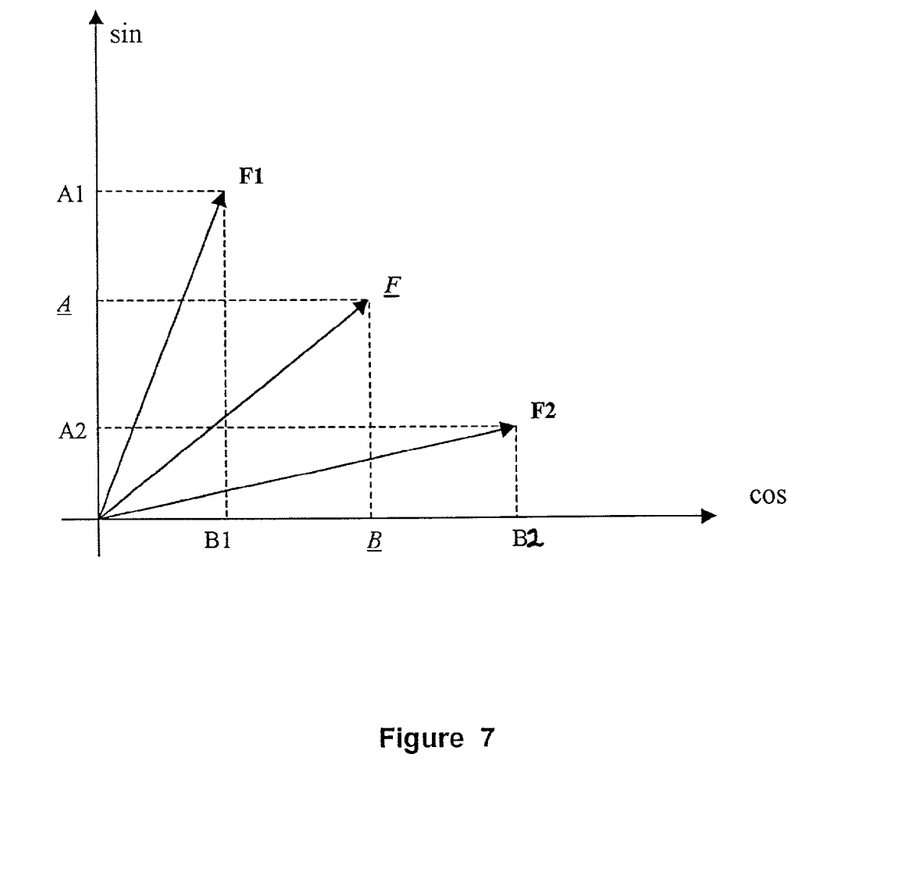
FIG. 7 is a graphical illustration showing vector summation used in the invention.

If the required number of good (error free data) samples has been achieved, the process proceeds to step 114 to determine if the VEP error free data passes a scattering check. The process of the scattering check is illustrated in FIG. 6 where the first step 301 is to select data from a number of samples of data corresponding to a series of visual stimuli displayed to the patient. In the case illustrated, five samples (i.e. data resulting from the display of five series of visual patterns) are chosen. At step 302, an algorithm is used to calculate the mean values of a selected particular Fourier component of the VEP that is of interest. The particular Fourier component of interest will be expressed as a vector which has amplitude and a phase, and the mean value of all of the chosen samples is determined by vector summation. For example, FIG. 7 illustrates vector summation for two vectors and shows the mean of two Fourier components in perpendicular coordinates. A1 and B1 are the sine and cosine amplitudes respectively of the first Fourier component F1; A2 and B2 are the sine and cosine amplitudes respectively of the second Fourier component F2. $\underline{A}$ and $\underline{B}$ are the sine and cosine amplitudes of the mean Fourier component $\underline{F}$. $\underline{A}$ is the average value of A1 and A2, and $\underline{B}$ is the average value of B1 and B2. A Fourier component at frequency ω can be expressed as the sum of a sine signal and a cosine signal as F(ω)=A sin ωt+B cos ωt; where A is the amplitude of the sine signal, and B is the amplitude of the cosine signal. Assume the mean of Fourier components in "n" VEP samples at frequency ω is $\underline{F}$(ω)=$\underline{A}$ sin ωt+$\underline{B}$ cos ωt. Then, $\underline{A}$=1/n*ΣAi; and $\underline{B}$=1/n *ΣBi. That is, the amplitudes of the mean are the average amplitudes of each individual Fourier component. At step 303, an analysis is conducted to determine if the distance between the mean value of the Fourier component of interest and each sample is within a predetermined distance from the mean value. The distance between the mean and individual Fourier component is defined as $$D=\sqrt{(Ai-\underline{A})^2+(Bi-\underline{B})^2}$$

where D is the distance; Ai and Bi are the amplitudes of sin and cos respectively of the Fourier component; and $\underline{A}$ and $\underline{B}$ are the amplitudes of sin and cos respectively of the mean. The predetermined distance is established by a well-known algorithm, known as the Mahalanobis-distance algorithm. (See "Applied Multivariate Statistics for the Social Sciences", $3^{rd}$ Edition, by James Stevens, Lawrence Erlbaum Associates, Mahwah, N.J., 1996.) If a particular sample, i.e. VEP data that results from one of the six displayed patterns of a series, is within the critical predetermined distance from the mean value, then that sample will be marked as a good sample, as indicated at step 304. If all of the samples have not been checked, as determined at step 305, then the scattering check process will be repeated, as indicated by the path 310. A new set of samples will then be reviewed from the total number of samples generated to be analyzed (which samples are stored in the CPU memory) for its mean value. If, however, all of the combinations among the samples have been checked and contain good data, the sample with the smallest distance from the mean value can be chosen as the good set of VEP samples and the scattering check will be successfully completed. Upon completion of the scattering check, the fault detection process will also be completed. If the scattering check has not been able to identify good data, sampling for new data will have to again proceed through step 112.

Figure 8:
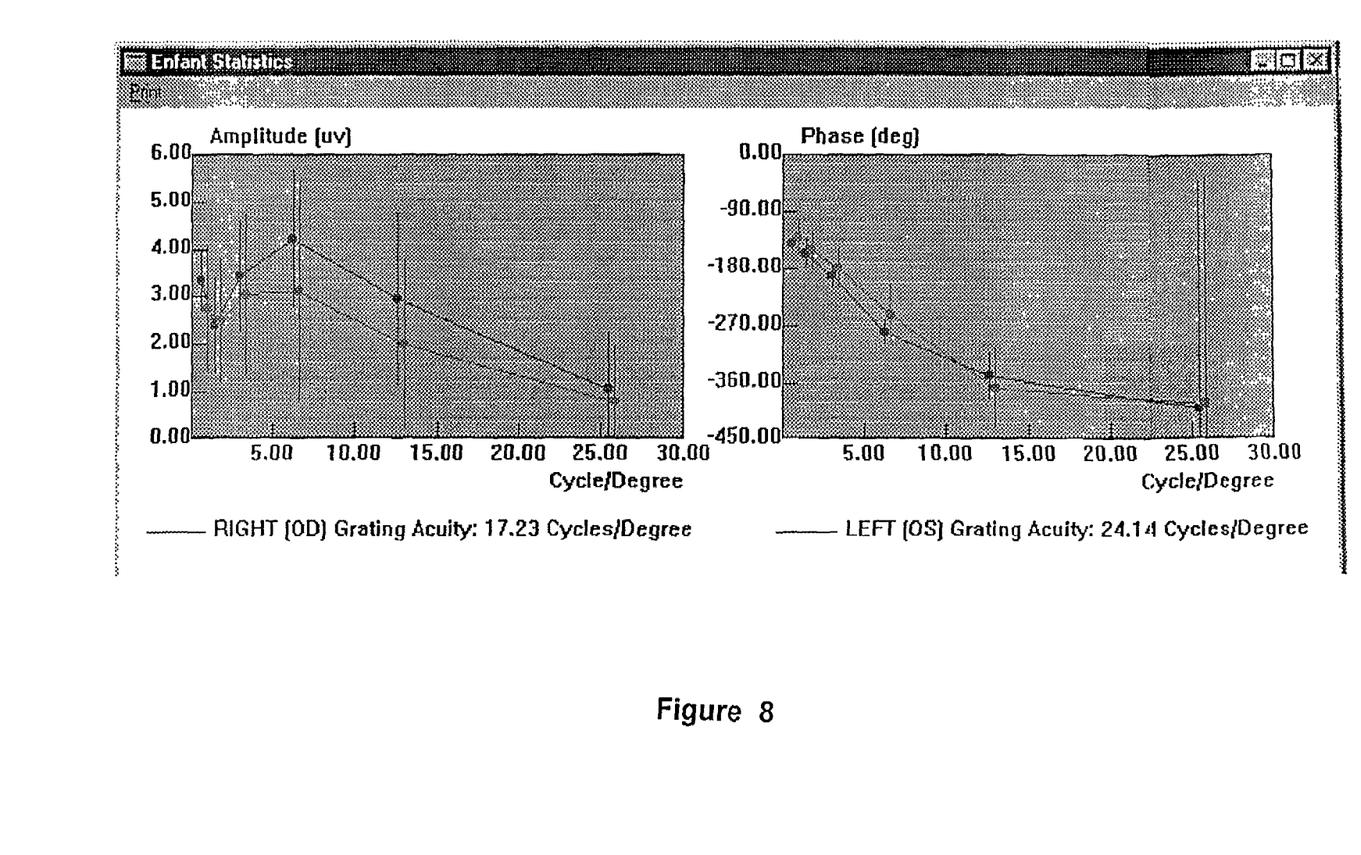
FIG. 8 is an example of plotted VEP data.

The results of the tests are displayed on the monitor 15 both graphically and textually. One of the graphs displayed will represent the amplitude of the patient's response at each spatial frequency for both eyes. FIG. 8 is a plot of measured VEP corresponding to six patterns with different spatial frequencies, for both left and right eyes of a patient. The plots show the amplitudes and phases of Fourier components at 15 Hz measured from both eyes. The dots are the mean values of the Fourier components. The error bars represent the variance of 95% confidence level in terms of F statistics. The graph represents the phase of the patient's response at each spatial frequency for both eyes. Text may also be presented to the operator to illustrate at which spatial frequency the two eyes have significantly different responses. This information is important for referral to an appropriate physician.

The results of the tests are computed using a discrete Fourier transform (DFT) and Tcirc$^2$ statistics. T circle statistics are known to those skilled in the art, particularly see "A New Statistic for Study State Evoked potentials" by J. Victor and J. Mast, Electroencphalogr Clin Neurophysiol, 1991; 78: 378-88. The DFT is used to extract the second harmonic of the patient's cortical response and the Tcirc$^2$ statistic is used to calculate whether the patient's brain responds at a certain spatial frequency is significantly different than random cortical activity using a 95% confidence level. The Tcirc$^2$ statistic for two samples is what determines whether significant differences exist between the two eyes of the patient at spatial frequencies tested.

After the results are displayed, the GUI allows the operator to clear the patient's data and start a new test.

The invention has been described and illustrated in connection with certain preferred embodiments which illustrate the principals of the invention. However, it should be understood that various modifications and changes may readily occur to those skilled in the art, and it is not intended to limit the invention to the construction and operation of the embodiments shown and described herein. Accordingly, additional modifications and equivalents may be considered as falling within the scope of the invention as defined by the claims herein below.

What is claimed is:

1. A system for performing a medical examination comprising:
   means for presenting a series of sensory stimuli for perception by a patient;
   means for detecting electrical signals representative of the patient's evoked brain potentials in response to said sensory stimuli, comprising a plurality of electrodes configured to be connected to a scalp of the patient, wherein at least one electrode is configured to be placed over a visual cortex of the patient;
   means for amplifying said signals, connected to said means for detecting;
   means for converting said signals into digitized data, connected to said means for amplifying;
   means for recording said data, connected to said means for converting;
   means for measuring said data, connected to said means for recording; and
   a computer processor programmed to analyze said data and to compare said data to predetermined values to determine if said data is outside of predetermined ranges and thus indicates unreliable data results, connected to said means for measuring and to said means for recording,
   wherein said means for recording records each occurrence of data being outside of predetermined ranges,
   wherein said computer processor is programmed with a predetermined maximum value of a plurality of faults and is further programmed to continue to collect data notwithstanding detection of a fault until after determining said predetermined maximum value of said plurality of faults and is programmed to stop the collection of data after receiving an indication that the data collected is reliable, and
   wherein said computer processor is further programmed, upon stopping a collection of data after receiving said indication that the data collected is reliable, to determine if said data passes a scattering check.

2. The system according to claim 1, wherein said means for presenting said series of sensory stimuli comprises a computer controlled visual stimulus generating device.

3. The system according to claim 1, wherein said means for converting said signals into digital data comprises an analog to digital converter.

4. The system according to claim 3,
   wherein said computer processor further executes a computer program comprising algorithms for determining whether said electrical signals reach a maximum value of the output of said means for amplifying said electrical signals, and for determining if the Fourier component of said electrical signals at 60 Hz exceeds a threshold value, and for determining if said data abruptly jumps beyond predetermined ranges.

5. The system according to claim 1, wherein said computer processor further executes a computer program comprising algorithms, the computer processor programmed to determine whether said electrical signals reach a maximum value output of said means for amplifying said electrical signals according to said algorithms.

6. The system according to claim 5, wherein said means for recording records the occurrence of one of said electrical signals reaching said maximum output value.

7. The system according to claim 1, wherein said computer processor further executes a computer program comprising algorithms, the computer processor programmed to determine if the Fourier component of said electrical signals at 60 Hz exceeds a threshold value according to said algorithms.

8. The system according to claim 7, wherein said means for recording records the occurrence of the Fourier component of one of said electrical signals at 60 Hz exceeding said threshold value.

9. The system according to claim 1, wherein said computer processor further executes a computer program comprising algorithms, the computer processor programmed to determine if said data abruptly jumps beyond predetermined ranges according to said algorithms.

10. The system according to claim 9, wherein said means for recording records the occurrence of said data abruptly jumping beyond said predetermined ranges.

11. The system according to claim 1, wherein said wherein said computer processor further executes a computer program comprising algorithms, the computer processor programmed to determine whether said electrical signals drift by using an average algorithm to smooth out said electrical signals over a period of time resulting in a curve of average signals versus time, integrating each segment of said curve and determining if the maximum value after segment integration exceeds a threshold value according to said algorithms.

12. The system according to claim 11, wherein said means for recording records the occurrence of said electrical signals drifting.

13. The system of claim 1, the system further comprising a hood placed between the patient and said means for presenting.

14. The system of claim 1, wherein said series of sensory stimuli comprises a series of six patterns of alternating and contrasting horizontally-oriented light and dark bands, wherein each pattern differs from other patterns by a thickness of each band.

* * * * *